(12) United States Patent
Nakamura et al.

(10) Patent No.: US 7,202,374 B2
(45) Date of Patent: Apr. 10, 2007

(54) FULLERENE DERIVATIVES AND THEIR METAL COMPLEXES

(75) Inventors: Eiichi Nakamura, 5-3-3-1001, Honkomagome, Bunkyo-ku, Tokyo (JP) 113-0021; Yutaka Matsuo, Tokyo (JP)

(73) Assignees: Mitsubishi Chemical Corporation, Tokyo (JP); Eiichi Nakamura, Tokyo (JP)

( * ) Notice: Subject to any disclaimer, the term of this patent is extended or adjusted under 35 U.S.C. 154(b) by 0 days.

(21) Appl. No.: 11/149,196

(22) Filed: Jun. 10, 2005

(65) Prior Publication Data

US 2005/0234252 A1   Oct. 20, 2005

Related U.S. Application Data

(62) Division of application No. 10/350,233, filed on Jan. 24, 2003, now Pat. No. 6,969,772.

(30) Foreign Application Priority Data

Jan. 24, 2002 (JP) .............................. 2002-016144

(51) Int. Cl.
*C07F 7/26* (2006.01)
(52) U.S. Cl. .................... 556/9; 556/465; 260/665; 585/26
(58) Field of Classification Search .............. 556/9, 556/465; 260/665; 585/26
See application file for complete search history.

(56) References Cited

U.S. PATENT DOCUMENTS

2005/0008558 A1   1/2005   Nakamura et al.

FOREIGN PATENT DOCUMENTS

| JP | 07 089972 | | 4/1995 |
|---|---|---|---|
| JP | 07089972 | * | 4/1995 |
| JP | 10-167994 | | 6/1998 |
| JP | 11-255508 | | 9/1999 |
| JP | 11-255509 | * | 9/1999 |
| JP | 2002-241323 | | 8/2002 |

OTHER PUBLICATIONS

Nagashima et al., Preparation of silylmethylated fullerenes and their application to synthesis of organic and inorganic fullerene derivatives, Nippon Kagaku Kaishi (1997), (2), 91-99.*
Nagashima et al., Electronic structures and redox properties of silyimethylated C60, Tetrahedron (1996), 52(14), 5053-64.*
Nagashima et al., Silylmethylations of C60 with Grignard Reagents: Selective Synthesis of HC60CH2SiMe2Y and C60(CH2SiMe2Y)2 with Selection of Solvents, Journal of Organic Chemistry (1994}, 59(6), 1246-1248.*
H. Nagashima, et al., Chemistry Letters, No. 6, XP-009018165, pp. 469-470, "Efficient Photooxygenation of Olefins by a $C_{60}$ Derivative Bearing an Organofluorine Tail", 1999.

H. Nagashima, et al., Tetrahedron, vol. 52, No. 14, XP-004104260, pp. 5053-5064, "Electronic Structures and Redox Properties of Silylmethylated $C_{60}$", 1996.
H. Nagashima, et al., Journal of Organic Chemistry, vol. 60, No. 16, XP-002258204, pp. 4966-4967, "Chlorosilanes and Silyl Triflates Containing $C_{60}$ as a Partial Structure. A Versatile Synthetic Entry Linking the $C_{60}$ Moieties With Alcohols, Phenols, and Silica", Aug. 11, 1995.
K. Fujiwara, et al., Tetrahedron, vol. 54, No. 10, XP-004109543, pp. 2049-2058, "Synthesis of a Propargyl Alcohol Having a $C_{60}$ Cage, its Transformation Into $C_{60}$ Derivatives With Polar Functional Groups, and the Solubility Measurements", Mar. 5, 1998.
J-P. Bourgeois, et al., Helvetica Chimica Acta, vol. 84, XP-002258206, pp. 1207-1226, "Hexakis-Adducts of [60] Fullerene With Different Addition Patterns: Templated Synthesis, Physical Properties, and Chemical Reactivity", May 16, 2001.
S. M. Draper, et al., Journal of Organometallic Chemistry, vol. 589, XP-002258207, pp. 157-167, "Novel Acetylene-Linked Di-Cobalt and Tetra-Cobalt Carbonyl Clusters", Nov. 5, 1999.
J-F. Nierengarten, et al., Helvetica Chimica Acta, vol. 80, No. 1, XP-009018170, pp. 293-316, "25. Methanofullerene Molecular Scaffolding: Towards $C_{60}$-Substituted Poly(Triacetylenes) and Expanded Radialenes, Preparation of a $C_{60}$—$C_{70}$ Hybrid Derivative, and a Novel Macrocyclization Reaction", 1997.
P. Timmermann, et al., Helvetica Chimica Acta, vol. 79, XP-009018169, pp. 6-20, "2. Fullerene-Acetylene Molecular Scaffolding: Chemistry of 2-Functionalized 1-Ethynylated $C_{60}$. Oxidative Homocoupling, Hexakis-Adduct Formation, and Attempted Synthesis of $C^{2-}_{124}$", 1996.
Gendai Kagaku (Modern Chemistry), Apr. 1992, p. 12.
Gendai Kagaku (Modern Chemistry), Jun. 200, p. 46.
N. Martin, et al., "C60-Based Electroactive Organofullerenes", Chem. Rev., vol. 98, (1998, pp. 2527-2547).
M. Sawamura, et al., "The First Pentahaptofullerene Metal Complexes", J. Am. Soc. vol. 118, (1996, pp. 12850-12851).
M. Sawamura, et al., "Stepwise Synthesis of Fullerene Cyclopentadienide R5C60—and Indenide R3C60 -, An Approach to Fully Unsymmetrically Substituted Derivatives", Organic Letters, vol. 2, No. 13, (Apr. 27, 200, pp. 1919-1921).
M. Sawamura, et al., "Pentaorgano[60] fullerence R5C60 -. A Water Soluble Hydrocarbon Anion", Chemistry Letters, (2000, pp. 1098-1099).

(Continued)

*Primary Examiner*—James O. Wilson
*Assistant Examiner*—CChukwuma Nwaonicha
(74) *Attorney, Agent, or Firm*—Oblon, Spivak, McClelland, Maier & Neustadt, P.C.

(57) ABSTRACT

A metal complex contains at least one ligand, each having the form of a molecule of a fullerene derivative or an anion of the fullerene derivative, where the fullerene derivative, with a solubility in n-hexane of not lower that 0.1 mg/ml at 250° C., includes a fullerene skeleton and three or more organic groups attached to the fullerene skeleton, where each of the organic groups is represented by the general formula (III):

$$—CH_2—X(R_2)(R_3)(R_4) \qquad (III)$$

where X represents an element belonging to the group 14 in the periodic table; and $R_2$, $R_3$ and $R_4$ may be the same or different and each represents a hydrogen atom, hydrocarbon group, alkoxy group or amino group.

13 Claims, No Drawings

OTHER PUBLICATIONS

M. Sawamura, et al., "Synthesis of π-Idenyl-type Fullerene Ligand and Its Metal Complexes via Quantitative Trisarylation of C70", J. Am. Chem. Soc. vol. 120, (1998, pp. 8285-8286).

H. Nagashima, et al., "Silylmethylations of C60 with Grignard Reagents: Selective Synthesis of HC60CH60CH2SiMe2Y and C60(CH2SiMe2Y)2 with Selection of Solvents", J. Org. Chem. vol. 59, (1994, pp. 1246-1248).

Gendai Kagaku (Modern Chemistry), Jun. 2000, p. 46.

N. Martin, et al., "C60-Based Electroactive Organofullerenes", Chem. Rev., v. 98 (1998), pp. 2527-2547.

M. Sawamura, et al., "The First Pentahaptofullerene Metal Complexes", J. Am. Chem. Soc. v. 118 (1996), pp. 12850-12851.

Patent Abstracts of Japan, JP 07-089972, Apr. 4, 1995.

H. Nagashima, et al., Chemistry Letters., No. 6, XP-009018165, pp. 469-470, "Efficient Photooxygenation of Olefins by a $C_{60}$ Derivative Bearing an Organofluorine Tail", (1999).

H. Nagashima, et al. Tetrahedron, v. 52, No. 14 XP-004104260, pp. 5053-5064, "Electronic Structures and Redox Properties of Silymethylated $C_{60}$" (1996).

H. Nagashima, et al., J. Org. Chem., v. 60, No. 16, XP-002258204, pp. 4966-4967, "Chlorosilanes and Silyl Triflates Containing $C_{60}$ as a Partial Structure. A Versatile Synthetic Entry Linking the $C_{60}$ Moieties with Alcohols, Phenols, and Silica", Aug. 11, 1995.

K. Fujiwara, et al., Tetrahedron, v. 54, No. 10, XP-004109543, pp. 2049-2058, "Synthesis of a Propargyl Alcohol Having a $C_{60}$ Cage, its Transformation into $C_{60}$ Derivatives with Polar Functional Groups, and the Solubility Measurements", Mar. 5, 1998.

J. Bourgeois, et al., Helvetica Chimica Acta, v. 84, XP-002258206, pp. 1207-1226 "Hexakis-Adducts of [60] Fullerene With Different Addition Patterns: Templated Synthesis, Physical Properties, and Chemical Reactivity", May 16, 2001.

S. M. Draper, et al., J. Organometallic Chem., v. 589, XP-002258207, pp. 157-167, "Novel Acetylene-Linked Di-Cobalt And Tetra-Cobalt Carbonyl Clusters", Nov. 5, 1999.

J. Nierengarten, et al., Helvetica Chimica Acta, v. 80, No. 1, XP-009018170, pp. 293-316, "25. Methanofullerene Molecular Scaffolding: Towards $C_{60}$-Substituted Poly(triacetylenes) And Expanded Radialenes, Preparation of a $C_{60}$—$C_{70}$ Hybrid Derivative, and A Novel Macrocyclization Reaction", (1997).

P. Timmermann, et al., Helvetica Chimica Acta, v. 79, XP-009018169, pp. 6-20, "2. Fullerene-Acetylene Molecular Scaffolding:Chemistry of 2-Functionalized 1-Ethynylated $C_{60}$ Oxidative Homocoupling, Hexakis-Adduct Formation, and Attempted Synthesis of $C^{2-}_{124}$", (1996).

M. Sawamura, et al., "Stepwise Synthesis of Fullerene Cyclopentadienide $R_5C_{60}$- and Indenide $R_3C_{60}$-. An Approach to Fully Unsymmetrically Substituted Derivatives", Org. Letters, v. 2, No. 13, pp. 1919-1921, Apr. 27, 2000.

Nagashima, et al., "Silylmethylations of $C_{60}$, with Grignard Reagents: Selective Synthesis of $HC_{60}CH_2SiMe_2Y$ and $C_{60}(CH_2SiMe_2Y)_2$ with Selection of Solvents", J. Org. Chem., v.59 (1994) pp. 1246-1248.

E. Allard, et al., "Chemical Generation and Reactivity of $C_{60}^{2-}$. High-yield and Regioselective Alkylation of [60, $1_n$] Fullerene", Tetrahedron Letters, v. 40 (1999), pp. 7223-7226.

M. Sawamura, et al., "Pentaorgano[60]fullerene $R_5C_{60}$-. A Water Soluble Hydrocarbon Anion", Chem. Letters, (2000) pp. 1098-1099.

M. Sawamura, et al., Synthesis of π-Idenyl-type Fullerene Ligand and Its Metal Complexes via Quantitative Trisarylation of $C_{70'}$, J. Am. Chem. Soc. v. 120, (1998) pp. 8285-8286.

* cited by examiner

FULLERENE DERIVATIVES AND THEIR METAL COMPLEXES

FIELD OF THE INVENTION

The present invention relates to a fullerene derivative having an extremely high solubility in an organic solvent and a metal complex comprising a molecule and/or anion of fullerene derivative as a ligand.

BACKGROUND OF THE INVENTION

Since a method for the synthesis of a large amount of $C_{60}$ was established in 1990, extensive studies have been made of fullerene. As a result, numerous fullerene derivatives have been synthesized and their various functions have been made obvious. With this technical progress, the development of various uses of electronic conductor, semiconductor, bioactive material, etc. comprising fullerene derivatives has been under way (for general remarks, see "Gendai Kagaku (Modern Chemistry)", April 1992, page 12, and June 2000, page 46, Chem. Rev., 1998, 98, 2527, etc.).

The inventors have synthesized various fullerene compounds comprising ten organic groups connected to the fullerene skeleton (hereinafter occasionally referred to as "derivative bearing 10 attached organic groups" or "10-fold adduct") and various fullerene compounds comprising five organic groups connected to the fullerene skeleton (hereinafter occasionally referred to as "derivative bearing 5 attached organic groups" or "5-fold adduct") and reported them (see Japanese Patent Laid-Open No. 1998-167994, Japanese Patent Laid-Open No. 1999-255509, Japanese Patent Laid-Open No. 2002-241323, J. Am. Chem. Soc. 1996, 118, 12850, Org. Lett. 2000, 2, 1919, Chem. Lett. 2000, 1098). The inventors have also synthesized fullerene compounds comprising three organic groups connected to the fullerene skeleton (hereinafter occasionally referred to as "derivative bearing 3 attached organic groups" or "3-fold adduct") and reported these compounds, including their metal complexes, separately of the aforementioned fullerene compounds (see Japanese Patent Laid-Open No. 1999-255508, J. Am. Chem. Soc. 1998, 120, 8285, Org. Lett. 2000, 2, 1919.).

In order to apply fullerene derivatives to various purposes, it is extremely useful to render them soluble in an organic solvent. It is thought that a fullerene derivative having a high solubility in an organic solvent, if obtained, can be applied to uses requiring dissolution in an organic solvent such as intermediate which is subjected to further transformation to synthesize other derivatives, electronic industrial material and ligand of metal complex, making it possible to drastically expand the application of fullerene derivatives.

However, all various known fullerene derivatives, including those disclosed in the above cited references, have an extremely low solubility in an ordinary organic solvent having a relatively small polarity. It is thus disadvantageous in that the solvent applicable when these fullerene derivatives are applied to the aforementioned various purposes is restricted, making the application of these fullerene derivatives extremely difficult or substantially impossible. Under these circumstances, a fullerene derivative having a high solubility in an organic solvent has been desired.

SUMMARY OF THE INVENTION

The invention has been worked out in the light of the aforementioned problems. An aim of the invention is to provide a fullerene derivative having a high solubility in an ordinary organic solvent and a metal complex comprising as a ligand, a molecule and/or anion of such a fullerene derivative.

The inventors made extensive studies of fullerene derivatives having an improved solubility in an organic solvent to solve the aforementioned problems. As a result, it was found that a fullerene derivative having a specific organic group exhibits an extremely high solubility in an organic solvent. The invention has thus been worked out.

In other words, the essence of the invention lies in a fullerene derivative having a solubility in n-hexane of not lower than 0.1 mg/ml at 25° C. and a metal complex comprising a molecule and/or anion of fullerene derivative as a ligand and having a solubility in n-hexane of not lower than 0.1 mg/ml at 25° C.

DETAILED DESCRIPTION OF THE INVENTION

The invention will be further described hereinafter.

The fullerene derivative of the invention is a compound which is derived from fullerene and has an extremely high solubility in an organic solvent.

The term "fullerene" as used herein is meant to indicate a carbon cluster comprising carbon atoms in a spherical or Rugby ball configuration. Specific examples of fullerene include $C_{60}$ (so-called Buckministerfullerene), $C_{70}$, $C_{76}$, $C_{78}$, $C_{82}$, $C_{84}$, $C_{90}$, $C_{94}$, $C_{96}$ and higher carbon clusters. The fullerene which is the skeleton of the fullerene derivative of the invention is not specifically limited. From the standpoint of availability of reactive starting materials to be used for production, $C_{60}$ or $C_{70}$ is desirable. The method for the production of fullerene is not specifically limited. Fullerenes produced by any known methods can be used as starting materials of fullerene derivatives. The fullerene of the invention may be a purified single compound or a mixture of two or more fullerenes.

The term "organic solvent" as used herein is meant to indicate a solvent which belongs to the group of organic compounds and is generally used for the dissolution of organic materials. Specific examples of the organic solvent include hydrocarbons such as pentanes, hexanes, heptanes, benzene, toluene and xylenes, esters such as methyl acetate, ethyl acetate, methyl propionate and ethyl propionate, ethers such as diethyl ether, dibutyl ether and tetrahydrofuran, halohydrocarbons such as dichloromethane, chloroform, dichloroethanes, chlorobenzene and dichlorobenzenes, alcohols such as methanol, ethanol and butanols, amides and ureas such as N,N-dimethylformamide, N,N,N',N'-tetramethylurea and γ-butyrolactam, and mixed solvents of two or more thereof.

The fullerene derivative of the invention has a high solubility in all or some of the aforementioned organic solvents. In order to secure the specific objectivity, the solubility in n-hexane as one of organic solvents at 25° C. is employed as a parameter showing solubility in organic solvent that defines the fullerene derivative of the invention.

The solubility in n-hexane at 25° C. is determined as follows. In some detail, a predetermined amount of n-hexane is added to a fullerene derivative. The mixture is then stirred at 25° C. for 1 hour. The resulting slurry is then subjected to centrifugal separation. The solution is then decanted. The solvent is then distilled off the resulting supernatant liquid. The resulting precipitate is dried in vacuo, and then measured for weight. Thus, the solubility in n-hexane at 25° C. is calculated.

The fullerene derivative of the invention is characterized in that it normally has a solubility in n-hexane of not lower than 0.1 mg/ml, preferably not lower than 1 mg/ml, more preferably not lower than 10 mg/ml, particularly not lower than 50 mg/ml at 25° C. as determined according to the aforementioned method.

The fullerene derivative of the invention is not limited in its structure so far as it has a solubility falling within the above defined range. A specific preferred example of the fullerene derivative is a fullerene derivative comprising one organic group or a plurality of organic groups added to the fullerene skeleton (hereinafter occasionally referred to as "adduct", "added derivative" or hereinafter occasionally referred to as "3-fold adduct", "5-fold adduct" or "10-fold adduct" depending upon the number of organic groups added to the fullerene skeleton (prefix number represents the number of organic groups added)). The term "organic group" as used herein is a general term for groups containing carbon. The term "addition" as used herein is meant to indicate the addition of groups to the bond in the fullerene skeleton resulting in the formation of a bond.

The aforementioned fullerene derivative comprising one organic group or a plurality of organic groups added to the fullerene skeleton will be further described hereinafter.

The kind of the organic groups to be added to the fullerene skeleton (hereinafter occasionally referred to as "attached organic group") is not specifically limited, but various organic groups may be used. In practice, however, organic groups having a structure mainly composed of a hydrocarbon some of the carbon atoms of which are optionally replaced by elements other than carbon belonging to the group 14 in the periodic table (18-group long form of the periodic table), particularly silicon, are used. The number of atoms including carbon belonging to the group 14 is preferably large. In some detail, it is preferred that four or more atoms be present per attached organic group. In particular, the sum of the number of carbon and silicon atoms is preferably from 4 to 20, more preferably from 5 to 18. The attached organic group may contain hetero-substituents such as halogen group, alkoxy group and amino group.

Attached organic groups mainly composed of aliphatic hydrocarbon structure tend to exhibit a higher solubility in an organic solvent than attached organic groups mainly composed of aromatic hydrocarbon structure even if the added number of attached organic groups are the same. Another tendency is that the more branches the attached organic group has, the higher is the solubility of the adduct in an organic solvent.

The attached organic group in the fullerene derivative of the invention is preferably an organic group which is connected to the fullerene skeleton via methylene group, i.e., organic group having the following structure:

   (I)

wherein $R_1$ represents a hydrogen atom or organic group.

The reason why the structure represented by the general formula (I) is desirable is uncertain. However, the reason is presumably because the methylene group present in the bond to the fullerene skeleton allows free rotation of $R_1$, thereby preventing the fullerene derivative molecules from approaching each other in the organic solvent and hence from undergoing molecular interaction.

In particular, $R_1$ in the general formula (I) preferably has a structure represented by the following general formula (II). In other words, typical attached organic group in the fullerene derivative has following formula (III):

   (II)

   (III)

wherein X represents an atom belonging to the group 14 in the periodic table. Specific examples of this atom include C, Si, Ge, Sn, and Pb. Preferred among these atoms are C and Si, particularly Si. $R_2$, $R_3$ and $R_4$ each independently represents a hydrogen atom, hydrocarbon group, alkoxy group or amino group. Preferably, all of $R_2$, $R_3$ and $R_4$ are elements other than hydrogen atom, i.e., hydrocarbon group, alkoxy group or amino group $R_2$, $R_3$ and $R_4$ may be the same or different.

The reason why the structure represented by the general formula (II) is desirable is uncertain. The reason is presumably because $R_2$, $R_3$ and $R_4$ occupy a relatively large space, thereby preventing the fullerene derivative molecules from approaching each other in the organic solvent and hence from undergoing molecular interaction.

Specific examples of the attached organic group in the fullerene derivative of the invention include n-pentyl group, isopentyl group, neopentyl group, 3-phenylpropyl group, 2,2-diethylpropyl group, (trimethylsilyl)methyl group, (phenyldimethylsilyl)methyl group, and (triethylsilyl)methyl group. Preferred among these attached organic groups are neopentyl group, (trimethylsilyl)methyl group, and (triethylsilyl)methyl group because they satisfy the general formula (I) and can be easily incorporated in the fullerene skeleton at a step during the synthesis of fullerene derivative. Particularly preferred among these attached organic groups are (trimethylsilyl)methyl group, and (triethylsilyl) methyl group because they also satisfy the general formula (II) or (III).

The number of these attached organic groups to be added to the fullerene skeleton is not specifically limited but may be arbitrarily selected from the group consisting of 1 or more. It is preferred that the number of attached organic groups to be added to the fullerene skeleton be greater because the fullerene which is a skeleton can be easily rendered soluble in an organic solvent. In some detail, the number of attached organic groups to be added to the fullerene skeleton is preferably 3 or more. In particular, as described later, the number of attached organic groups to be added to the fullerene skeleton is preferably 3, 5 or 10 because derivative bearing 3 attached organic groups, derivative bearing 5 attached organic groups and derivative bearing 10 attached organic groups can be selectively synthesized by properly selecting the method for addition reaction. When the number of attached organic groups to be added to the fullerene skeleton is plural, these attached organic groups may be the same or different.

The fullerene derivative of the invention can be produced by any of various methods depending on its structure. For example, a fullerene derivative comprising one or a plurality of organic groups added to the fullerene skeleton (derivative bearing attached organic groups) can be produced by introducing organic groups into fullerene skeleton by various known methods.

The introduction of attached organic groups into fullerene can be effected by nucleophilic addition by way of example. In some detail, addition reaction may be effected in the presence of a Grignard reagent, an organolithium reagent or an organocopper reagent prepared from such a reagent and a copper compound at one step or multiple steps. The structure of Grignard reagent, organic lithium reagent and organocopper reagent are not specifically limited. In other words, a Grignard reagent or an organic lithium reagent having an organic group to be incorporated may be used to effect direct addition reaction. Alternatively, in the case where such a Grignard reagent or an organic lithium reagent can be difficultly synthesized or is unstable, a group which can be easily incorporated may be incorporated in the fullerene skeleton which is then subjected to conversion reaction so that the substituent is converted to the desired organic group. In the case where the organic group to be incorporated in the presence of such a reagent has a structure satisfying the general formula (I) or (II), it is more desirable that none of $R_2$, $R_3$ and $R_4$ be a hydrogen atom.

Numerous combinations of relative positions at which the organic groups are added to the fullerene skeleton are possible. The addition pattern is not specifically limited. However, it is known that as 3-fold adduct, 5-fold adduct and 10-fold adduct there can be selectively synthesized adducts having structures represented by the following general formulae (IV), (V) and (VI), respectively. Therefore, from the standpoint of ease of synthesis, adducts having these structures are preferably produced.

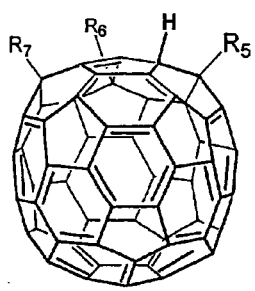

(IV)

wherein $R_5$ to $R_7$ may be the same or different and each independently represents an organic group.

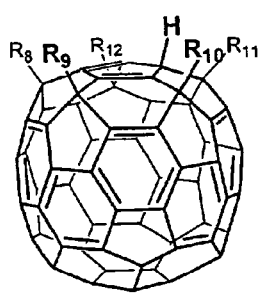

(V)

wherein $R_8$ to $R_{12}$ may be the same or different and each independently represents an organic group.

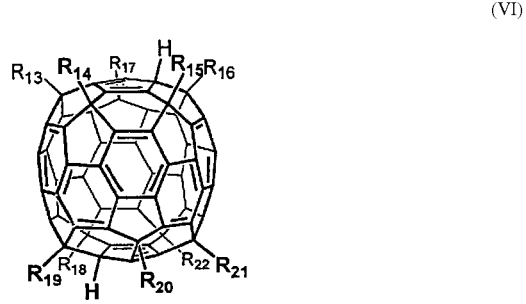

(VI)

wherein $R_{13}$ to $R_{22}$ may be the same or different and each independently represents an organic group.

In the case where addition reaction is effected in the presence of an organic copper reagent as shown by the following general formula (VII), the resulting primary product is presumably the corresponding organic copper compound. The fullerene derivative of the invention is isolated in the form of protonated compound normally by reacting this primary product with a protonic compound such as $H_2O$.

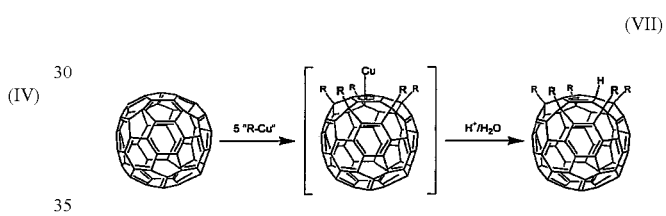

(VII)

(The general formula (VII) is illustrated with reference to the synthesis of 5-fold adduct of fullerene by way of example, but the invention is not limited to 5-fold adduct. Further, the general formula (VII) is illustrated with all of the attached organic groups added to the fullerene skeleton represented by R. The plurality of R's may be hereinafter the same or different unless otherwise specified.)

This protonated compound is a preferred embodiment of the fullerene derivative of the invention. The protonated compound which has once been isolated is then reacted with alkyllithium, etc. so that it is easily deprotonated to lithiated compound as represented by the following general formula (VIII). By adding an electrophilic reagent to this lithiated compound, it can be converted to another preferred form of fullerene derivative. For example, the lithiated compound can be alkylated with an alkylation reagent, etc. to an alkylated compound. These products obtained by electrophilic reaction, too, are other preferred embodiments of the fullerene derivative of the invention.

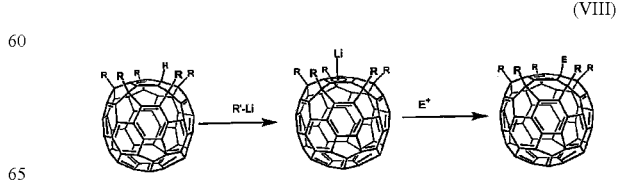

(VIII)

wherein E+ represents a reagent having electrophilic reactivity.

The fullerene derivative of the invention exhibits as an extremely a high solubility in an organic solvent as not lower than 0.1 mg/ml in n-hexane at 25° C. Therefore, when dissolved in an organic solvent, the fullerene derivative of the invention can be substantially handled in the same manner as for ordinary organic compounds. Further, the fullerene derivative of the invention can be used for purposes requiring dissolution in an organic solvent such as intermediate which is subjected to further transformation to synthesize other derivatives, electronic industrial material and ligand of metal complex and thus is extremely useful. Accordingly, the fullerene derivative of the invention can be expected to be widely applied to arts which have heretofore difficultly allowed the utilization of fullerene derivatives.

The metal complex comprising a molecule and/or anion of fullerene derivative as a ligand will be further described hereinafter. This metal complex has a molecule and/or anion of fullerene derivative as a ligand and exhibits a high solubility in an organic solvent. As a parameter of the solubility of the metal complex in an organic solvent, the solubility of the metal complex in n-hexane at 25° C. is defined to secure a specific objectivity as mentioned above. In some detail, the metal complex of the invention normally exhibits a solubility in n-hexane of not lower than 0.1 mg/ml, preferably not lower than 1 mg/ml at room temperature (typically 25° C.).

The metal complex of the invention is not limited in its structure and complex form so far as it exhibits a high solubility in an organic solvent as mentioned above. The metal complex of the invention preferably has a molecule and/or anion of the fullerene derivative of the invention as detailed above as a ligand. In particular, compounds comprising the aforementioned 3-fold adduct, 5-fold adduct or 10-fold adduct of fullerene having the following structure with cyclopentadienyl anion position are desirable from the standpoint of ease of synthesis.

(IX)

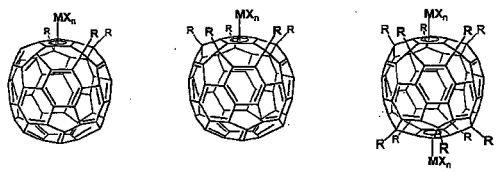

wherein MXn represents a metal fragment in which M represents a metal atom selected from the group consisting of alkali metal, alkaline earth metal, transition metal, Sn and Tl, X represents a ligand such as molecule or ion attached to the metal atom M, and n represents a number of not smaller than 0.

Specific examples of M include Li, Na, K, Ba, Sn, Sc, Ti, V, Cr, Mn, Fe, Co, Ni, Cu, Zn, Zr, Ru, Rh, Pd, Ag, Cd, Hf, Ta, W, Re, Pt, Au, Hg, Tl, and Sm. Preferred among these metal atoms are Li, K, Ba, Ti, Fe, Cu, Zr, Ru, Rh, Pd, and Hf.

Specific examples of X include neutral ligands including ethers such as THF (tetrahydrofuran) and dimethoxyethane, phosphines such as trimethylphosphine and triphenylphosphine, nitriles such as acetonitrile, CO and olefins such as ethylene and cyclooctadiene, halogen atoms such as Cl and Br, alkoxy groups such as hydride, methoxy, ethoxy and butoxy, amide groups such as dimethylamide and diethylamide, alkyl groups such as methyl, ethyl and butyl, phenyl group, substituted phenyl groups, and sulfonate groups such as tosylate.

The proper ligand X and the number n of the ligands X are determined by the properties and valency of the metal atom M. The plurality of X's, if any, may be the same or different.

The metal complex of the invention can be produced by various methods depending on the structure thereof. In some detail, a proper metal precursor can be acted on the lithiated compound of fullerene derivative represented by the general formula (VIII) as shown by the general formula (X) to synthesize a metal complex of the invention having a corresponding fullerene derivative as a ligand. The aforementioned lithiated compound itself, too, is an embodiment of the metal complex of the invention.

(X)

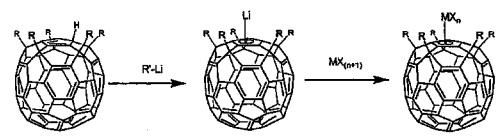

The metal complex of the invention has a molecule and/or anion of fullerene derivative as a ligand and thus is provided with inherent properties of fullerene derivative. The metal complex of the invention also exhibits as extremely a high solubility in an organic solvent as not lower than 0.1 mg/ml in n-hexane at 25° C. and thus can be used for various purposes requiring dissolution in an organic solvent and is extremely useful. Accordingly, the metal complex of the invention can be expected to be widely applied to arts which have heretofore difficultly allowed the utilization of fullerene derivatives.

The invention will be further described in the following examples, but the invention is not limited thereto so far as it does not depart from the scope thereof.

EXAMPLE 1

Synthesis of $C_{60}[CH_2Si(CH_3)_3]_5H$

As shown in Scheme 1, in an atmosphere of nitrogen, 100 mg of $C_{60}$ was dissolved in 15 ml of o-dichlorobenzene. The solution was then reacted with a copper reagent prepared from 16 equivalents of a trimethylsilylmethyl magnesium chloride Grignard reagent $(CH_3)_3SiCH_2MgCl$ in diethyl-ether (concentration: about 1.0 M) and 18 equivalents of a copper (I) bromide-dimethyl sulfide complex $CuBr.S(CH_3)_2$ at 0° C. After 1 hour, to the reaction solution was added 0.1 ml of a saturated aqueous ammonium chloride solution to quench the reaction. After the termination of the reaction, the reaction solution was concentrated to about 15 ml. The reaction solution was diluted with 50 ml of toluene, and then passed through a silica gel plug with toluene as an eluent to remove magnesium salts and other by-products. The solvent was then distilled off until about 2 ml of the solvent was left. To the reaction solution was then added 200 ml of methanol to cause reprecipitation. As a result, a 5-fold trimethylsilylmethyl adduct $(C_{60}[CH_2Si(CH_3)_3]_5H)$ having a purity of 97% was obtained (isolated yield: 97%).

Scheme 1

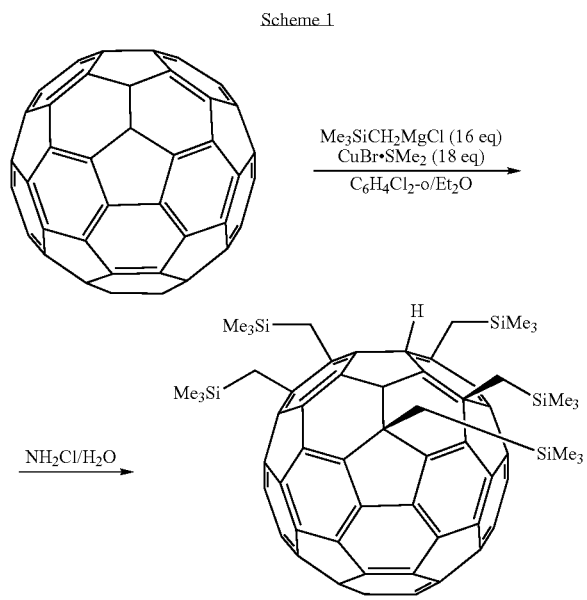

wherein Me represents a methyl group (—CH$_3$).

NMR Data of C$_{60}$[CH$_2$Si(CH$_3$)$_3$]$_5$H $^1$H-NMR (C$_6$D$_6$, 30° C.) 0.16 (s, 9H, Si(CH$_3$)$_3$), 0.21 (s, 18H, Si(CH$_3$)$_3$), 0.23 (s, 18H, Si(CH$_3$)$_3$), 2.10 (d, $^2J_{H-H}$=14.8 Hz, 2H, CH$_2$), 2.17 (s, 2H, CH$_2$), 2.18 (s, 2H, CH$_2$), 2.25 (s, 2H, CH$_2$), 2.34 (d, $^2J_{H-H}$=14.8 Hz, 2H, CH$_2$), 4.70 (s, 1H, H(Cp))

$^{13}$C-NMR (C$_6$D$_6$, 30° C.): 0.57 (Si(CH$_3$)$_3$) 0.57 (Si(CH$_3$)$_3$) 0.62 (Si(CH$_3$)$_3$) 31.55 (CH$_2$), 31.94 (CH$_2$), 38.71 (CH$_2$), 53.38 (CH$_3$C), 53.66 (CH$_3$C), 55.26 (CH$_3$C), 63.63 (HC(Cp)), 143.05, 143.87, 143.90, 144.11, 144.36, 144.65, 145.56, 145.63, 145.87, 146.37, 146.64, 147.23, 147.45, 147.52, 148.09, 148.12, 148.40, 148.59, 148.67, 149.03, 149.11, 149.26, 150.12, 150.88, 154.22, 154.46, 154.69, 157.88

Comparison of compounds which have been already known, i.e., C$_{60}$(CH$_3$)$_5$H and C$_{60}$(C$_6$H$_5$)$_5$H in signal of proton at cyclopentadiene moiety in CDCl$_3$ showed the following data:

C$_{60}$(CH$_3$)$_5$H, 4.46 ppm
C$_{60}$(CH$_2$Si(CH$_3$)$_3$)$_5$H, 4.56 ppm
C$_{60}$(C$_6$H$_5$)$_5$H, 5.30 ppm Properties of C$_{60}$[CH$_2$Si(CH$_3$)$_3$]$_5$H Brown powder. When it stayed solid, it was stable at room temperature in the air.

Solubility of C$_{60}$[CH$_2$Si(CH$_3$)$_3$]$_5$H

To 100 mg of C$_{60}$[CH$_2$Si(CH$_3$)$_3$]$_5$H was added 0.5 ml of n-hexane. The mixture was then stirred at 25° C. for 1 hour. The slurry was purified, and then subjected to centrifugal separation by a centrifugal separator. The resulting supernatant liquid was withdrawn. The solvent was then distilled off. The residue was then dried in vacuo. The weight of the residue was then measured. The result was 32.5 mg. Accordingly, the solubility of this compound in n-hexane at room temperature (25° C.) can be calculated to be 65 mg/ml.

EXAMPLE 2

Synthesis of C$_{60}$\{CH$_2$Si(CH$_3$)$_3$\}$_3$H

As shown in Scheme 2, in dried air, 0.5 g of C$_{60}$ was dissolved in 150 ml of o-dichlorobenzene. The solution was then reacted with 8 equivalents of a trimethylsilylmethyl magnesium chloride Grignard reagent (CH$_3$)$_3$SiCH$_2$MgCl in an ether (concentration: about 1.0 M) at room temperature (25° C.). After 2 hours, to the reaction solution was added 0.5 ml of a saturated aqueous ammonium chloride solution to quench excessive Grignard reagent. The solvent was then distilled off under reduced pressure at 70° C. The resulting precipitate was then dissolved in 100 ml of toluene. The reaction solution was then passed through a silica gel plug with toluene as an eluent to remove magnesium salts and other by-products. When toluene was distilled off, a 2-fold trimethylsilylmethyl adduct C$_{60}$\{CH$_2$Si(CH$_3$)$_3$\}$_2$ having a purity of 70% was obtained. The product was then extracted with hot n-hexane. As a result, substantially pure C$_{60}$\{CH$_2$Si(CH$_3$)$_3$\}$_2$ was obtained. The isolated yield was 54%.

In an atmosphere of argon, 170 mg of C$_{60}$\{CH$_2$Si(CH$_3$)$_3$\}$_2$ thus obtained was dissolved in 20 ml of o-dichlorobenzene. The reaction solution was then reacted with 5 equivalents of trimethylsilylmethyl magnesium chloride Grignard reagent ((CH$_3$)$_3$SiCH$_2$MgCl) in an ether (concentration: about 1.0 M) at room temperature (25° C.). After 1 hour, to the reaction solution was added 0.2 ml of a saturated aqueous ammonium chloride solution to quench the reaction. The solvent was then distilled off under reduced pressure at 70° C. The resulting precipitate was then dissolved in 20 ml of toluene. The reaction solution was then passed through a silica gel plug with toluene as an eluent to remove magnesium salt and other by-products. When toluene was then distilled off, a 3-fold trimethylsilylmethyl adduct C$_{60}$\{CH$_2$Si(CH$_3$)$_3$\}$_3$H having a purity of about 50% was obtained. The 3-fold trimethylsilylmethyl adduct was then subjected to fractionation with HPLC (eluent: toluene/2-propanol=7/3) equipped with a column (BuckyPrep, produced by Nacalai Tesque Co., Ltd.) to obtain pure C$_{60}$\{CH$_2$Si(CH$_3$)$_3$\}$_3$H. The isolated yield of C$_{60}$\{CH$_2$Si(CH$_3$)$_3$\}$_3$H from C$_{60}$\{CH$_2$Si(CH$_3$)$_3$\}$_2$ was 37%. The total yield of C$_{60}$\{CH$_2$Si(CH$_3$)$_3$\}$_3$H from C$_{60}$ was 20%.

Scheme 2

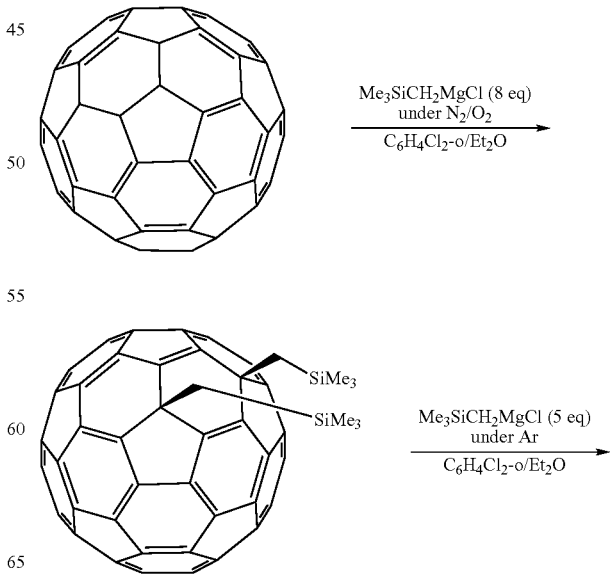

-continued

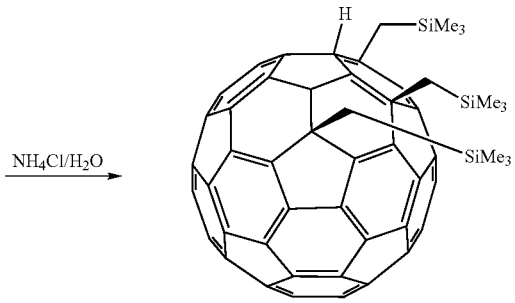

wherein Me represents a methyl group (—CH$_3$).

NMR data of C$_{60}${CH$_2$Si(CH$_3$)$_3$}$_3$H $^1$H-NMR (CDCl$_3$, 30° C.): 0.07 (s, 9H, Si(CH$_3$)$_3$), 0.21 (s, 18H, Si(CH$_3$)$_3$), 2.06 (d, $^2J_{H-H}$=14.4 Hz, 1H, CH$_2$), 2.24 (d, $^2J_{H-H}$=14.4 Hz, 1H, CH$_2$), 2.29 (d, $^2J_{H-H}$=14.4 Hz, 1H, CH$_2$), 2.29 (d, $^2J_{H-H}$=14.4 Hz, 1H, CH$_2$), 2.38 (d, $^2J_{H-H}$=14.4 Hz, 1H, CH$_2$), 2.40 (d, $^2J_{H-H}$=14.4 Hz, 1H, CH$_2$), 5.30 (s, 1H, H(Cp))

$^{13}$C-NMR (C$_6$D$_6$, 30° C.): 0.25 (q, $^1J_{C-H}$=129 Hz, Si(CH$_3$)$_3$), 0.30 (q, $^1J_{C-H}$=129 HZ, Si(CH$_3$)$_3$), 0.50 (q, $^1J_{C-H}$=129 Hz, Si(CH$_3$)$_3$), 31.21 (t, $^1J_{C-H}$=132 Hz, CH$_2$), 32.59 (t, $^1J_{C-H}$=132 Hz, CH$_2$), 38.08 (t, $^1J_{C-H}$=132 Hz, CH$_2$) 52.92 (s, CCH$_2$), 54.97 (s, CCH$_2$), 56.85 (s, CCH$_2$), 61.98 (d, $^1J_{C-H}$=136 Hz, HC(Ind)), 133.88–162.98

Properties of C$_{60}${CH$_2$Si(CH$_3$)$_3$}$_3$H

Brown powder. When it stayed solid, it was stable at room temperature in the air.

Solubility of C$_{60}${CH$_2$Si(CH$_3$)$_3$}$_3$H

The solubility of C$_{60}${CH$_2$Si(CH$_3$)$_3$}$_3$H in n-hexane at room temperature (25° C.) was measured under the same conditions as in Example 1. The result was 11 mg/ml.

EXAMPLE 3

Synthesis of Rh[C$_{60}${CH$_2$Si(CH$_3$)$_3$}$_3$](1,5-cyclooctadiene)

8.0 mg (0.0081 mmol) of the 3-fold adduct (C$_{60}${CH$_2$Si(CH$_3$)$_3$}$_3$H) of Example 2 was dissolved in 5.0 ml of THF. To the solution was then added a THF solution of 1.2 equivalents of potassium t-butoxide at room temperature. When the reaction mixture was stirred for 10 minutes, a green solution of C$_{60}${CH$_2$Si(CH$_3$)$_3$}$_3$K was produced. To the solution was then added 1.0 equivalent (4.0 mg or 0.0081 mmol) of {Rh(1,5-cyclooctadiene)Cl}$_2$ at room temperature. The reaction mixture was then stirred for 10 minutes. The solvent was then distilled off. The precipitate was then extracted with toluene to obtain a metal complex. Toluene was then distilled off. The resulting solid was then washed with n-hexane to obtain pure Rh[C$_{60}${CH$_2$Si(CH$_3$)$_3$}$_3$](1,5-cyclooctadiene). The isolated yield of Rh[C$_{60}${CH$_2$Si(CH$_3$)$_3$}$_3$](1,5-cyclooctadiene) from {C$_{60}$[CH$_2$Si(CH$_3$)$_3$]$_3$H was 91%.

NMR data of Rh[C$_{60}${CH$_2$Si(CH$_3$)$_3$}$_3$](1,5-cyclooctadiene)

$^1$H-NMR (CDCl$_3$, 30° C.): 0.08 (s, 9H, Si(CH$_3$)$_3$), 0.11 (s, 18H, Si(CH$_3$)$_3$), 1.77 (d, $^2J_{H-H}$=14 Hz, 2H, CH$_2$), 2.04 (d, $^2J_{H-H}$=14 Hz, 2H, CH$_2$), 2.43 (br s, 8H, cod), 2.44 (d, $^2J_{H-H}$=14 Hz, 2H, CH$_2$), 4.19 (br s, 2H, cod), 5.62 (br s, 2H, cod)

Other Data of Rh[C$_{60}${CH$_2$Si(CH$_3$)$_3$}$_3$](1,5-cyclooctadiene)

APCl-Mass (+) m/z=1194 (M$^+$)

UV-vis: λmax=705 nm

Solubility of Rh[C$_{60}${CH$_2$Si(CH$_3$)$_3$}$_3$](1,5-cyclooctadiene)

The solubility of Rh[C$_{60}${CH$_2$Si(CH$_3$)$_3$}$_3$](1,5-cyclooctadiene) in n-hexane at room temperature (25° C.) was measured under the same conditions as in Example 1. The result was 5.0 mg/ml.

COMPARATIVE EXAMPLE 1

The solubility of C$_{60}$ produced by Aldrich Co., Ltd. was measured under the same conditions as in Example 1. The result was less than 0.001 mg/ml. Thus, this product was little dissolved in n-hexane.

COMPARATIVE EXAMPLE 2

(C$_6$H$_5$)$_5$C$_{60}$H was synthesized according to the method described in Example 1 of Japanese Patent Laid-Open No. 1998-167994. The solubility of (C$_6$H$_5$)$_5$C$_{60}$H thus obtained was measured under the same conditions as in Example 1 of the invention. The result was less than 0.001 mg/ml. Thus, this product was little dissolved in n-hexane.

COMPARATIVE EXAMPLE 3

(CH$_3$)$_5$C$_{60}$H was synthesized according to the method described in Example 1 of Japanese Patent Laid-Open No. 1999-255509. The solubility of (CH$_3$)$_5$C$_{60}$H thus obtained was measured under the same conditions as in Example 1 of the invention. The result was less than 0.001 mg/ml. Thus, this product was little dissolved in n-hexane.

REFERENCE EXAMPLE 1

The solubility of C$_{60}$[CH$_2$Si(CH$_3$)$_3$]$_2$ (known in J. Org. Chem. 1994, 59, 1246), which is an intermediate product of Example 2, was measured under the same conditions as in Example 1. The result was about 0.05 mg/ml. The solubility of this intermediate product measured at 50° C. under the same conditions as in Example 1 was about 0.2 mg/ml. Thus, as described in Example 2, this fullerene derivative can be withdrawn by extraction with hot n-hexane.

The fullerene derivative of the invention exhibits as an extremely a high solubility in an organic solvent as not lower than 0.1 mg/ml in n-hexane at 25° C. Therefore, the fullerene derivative of the invention can be used for purposes requiring dissolution in an organic solvent such as intermediate which is subjected to further transformation to synthesize other derivatives, electronic industrial material and ligand of metal complex and thus is extremely useful.

The metal complex of the invention has a molecule and/or anion of fullerene derivative as a ligand and exhibits as extremely a high solubility in an organic solvent as not lower than 0.1 mg/ml in n-hexane at 25° C. Therefore, as a metal complex having functions characteristic to fullerene derivative, the metal complex of the invention can be used for various purposes requiring dissolution in an organic solvent such as catalyst and electronic industrial material and is extremely useful.

While the invention has been described in detail and with reference to specific embodiments thereof, it will be apparent to one skilled in the art that various changes and modifications can be made therein without departing from the spirit and scope thereof.

This application is based on Japanese patent application No. 2002-016144 filed on Jan. 24, 2002, the entire contents thereof being hereby incorporated by reference.

What is claimed is:

1. A metal complex comprising at least one ligand selected from the group consisting of a molecule of a fullerene derivative, and an anion of the fullerene derivative, wherein the fullerene derivative comprises
   a fullerene skeleton and
   three or more organic groups attached to the fullerene skeleton, wherein
   each of the organic groups is represented by the general formula (III):

$$-CH_2-X(R_2)(R_3)(R_4) \qquad (III)$$

where
   X represents an atom selected from the group consisting of Si, Ge, Sn and Pb;
   and
   $R_2$, $R_3$ and $R_4$ may be the same or different and each represents a hydrogen atom, hydrocarbon group, alkoxy group or amino group.

2. The metal complex according to claim 1, wherein the metal complex has a solubility in n-hexane of not lower than 0.1 mg/ml at 25° C.

3. The metal complex according to claim 2, wherein the solubility is not lower than 1 mg/ml.

4. The metal complex according to claim 2, wherein the fullerene skeleton is $C_{60}$.

5. The metal complex according to claim 1, wherein X is Si.

6. A fullerene derivative comprising
   a fullerene skeleton and
   three or more organic groups attached to the fullerene skeleton, wherein
   each of the organic groups is represented by the general formula (III):

$$-CH_2-X(R_2)(R_3)(R_4) \qquad (III)$$

where
   X represents an atom selected from the group consisting of Si, Ge, Sn and Pb;
   and
   $R_2$, $R_3$ and $R_4$ may be the same or different and each represents a hydrogen atom, hydrocarbon group, alkoxy group or amino group.

7. The fullerene derivative according to claim 6, wherein X is Si.

8. The fullerene derivative according to claim 6, having a solubility in n-hexane of not lower than 0.1 mg/ml at 25° C.

9. The fullerene derivative according to claim 8, wherein the solubility is not lower than 10 mg/ml.

10. The fullerene derivative according to claim 9, wherein the solubility is not lower than 50 mg/ml.

11. The fullerene derivative according to claim 8, wherein the fullerene skeleton is $C_{60}$.

12. A method of making a fullerene derivative, the method comprising
    attaching three or more organic groups to a fullerene skeleton; and
    producing the fullerene derivative of claim 6.

13. The method according to claim 12, wherein the attaching is by nucleophilic addition.

* * * * *